(12) United States Patent
Humbert et al.

(10) Patent No.: US 9,244,031 B2
(45) Date of Patent: Jan. 26, 2016

(54) GAS SENSOR

(75) Inventors: Aurelie Humbert, Brussels (BE); David Tio Castro, Oud-Heverlee (BE)

(73) Assignee: NXP, B.V., Eindhoven (NL)

( * ) Notice: Subject to any disclaimer, the term of this patent is extended or adjusted under 35 U.S.C. 154(b) by 611 days.

(21) Appl. No.: 13/557,042

(22) Filed: Jul. 24, 2012

(65) Prior Publication Data

US 2013/0042669 A1    Feb. 21, 2013

(30) Foreign Application Priority Data

Aug. 16, 2011  (EP) .................................. 11177642

(51) Int. Cl.
*G01N 27/12*  (2006.01)

(52) U.S. Cl.
CPC .................... *G01N 27/128* (2013.01)

(58) Field of Classification Search
CPC .................................................. G01N 27/128
See application file for complete search history.

(56) References Cited

U.S. PATENT DOCUMENTS

| | | | |
|---|---|---|---|
| 4,215,564 A | 8/1980 | Lawson et al. | |
| 4,349,808 A | 9/1982 | Kraus | |
| 4,580,439 A | 4/1986 | Manaka | |
| 4,967,589 A | 11/1990 | Yagawara et al. | |
| 5,597,953 A | 1/1997 | Usanov et al. | |
| 5,753,916 A | 5/1998 | Ooisi et al. | |
| 5,756,878 A | 5/1998 | Muto et al. | |
| 7,564,350 B2 | 7/2009 | Boman et al. | |
| 7,574,910 B2 * | 8/2009 | Manaka et al. | 73/204.26 |
| 7,670,046 B2 | 3/2010 | Mitov | |
| 8,393,196 B2 | 3/2013 | Ikawa et al. | |
| 8,452,489 B2 | 5/2013 | Marra | |
| 8,853,798 B2 | 10/2014 | Merz | |
| 2004/0251117 A1 | 12/2004 | Wong et al. | |
| 2006/0169024 A1 | 8/2006 | Shoji | |
| 2008/0311434 A1 * | 12/2008 | Rey-Mermet et al. | 429/12 |
| 2013/0032902 A1 | 2/2013 | Merz | |
| 2014/0102172 A1 | 4/2014 | Daamen et al. | |

FOREIGN PATENT DOCUMENTS

| | | |
|---|---|---|
| CN | 101578188 A | 11/2009 |
| CN | 201341166 Y | 11/2009 |
| CN | 102054303 A | 5/2011 |
| DE | 10 2006 009450 A1 | 9/2006 |

(Continued)

OTHER PUBLICATIONS

Nemoto Sensor Engineering Co, Ltd; NAP-21 Product Specification. Jun. 11, 2011. pp. 1-2.*

(Continued)

*Primary Examiner* — Lisa Caputo
*Assistant Examiner* — Punam Roy

(57) ABSTRACT

A gas sensor on a semiconductor substrate. The gas sensor includes an elongate sensor element extending across an opening and has first and second opposed surfaces exposed for contact with a gas to be sensed. The first surface faces away from a major surface of the substrate. The second surface faces toward said major surface. The electrical conductivity of the elongate sensor element is sensitive to a composition and/or concentration of said gas to which the opposed first and second surfaces are exposable. The gas sensor further includes a support structure arranged to increase the mechanical robustness of the gas sensor by supporting the elongate sensor element in the opening.

15 Claims, 5 Drawing Sheets

(56) References Cited

FOREIGN PATENT DOCUMENTS

| EP | 2 743 677 A1 | 6/2014 |
|---|---|---|
| EP | 2 853 889 A1 | 4/2015 |
| JP | 6-118046 A | 4/1994 |
| JP | 2005-003468 A | 1/2005 |
| WO | 2005/069597 A1 | 7/2004 |
| WO | 2009/138893 A1 | 11/2009 |

OTHER PUBLICATIONS

Liu, Lili, et al; "Coal Mine Security Intelligent Control System Based on RFID"; retrieved from the internet www.cnki.net; pp. 39-41 (Sep. 2004) No English version found.

Office Action from counterpart application CN201210286970.3 (Dec. 11, 2014).

Office Action from counterpart application CN 201210286970.3 (Apr. 23, 2014).

Datasheet, "Thermal Conductivity Sensor—MTCS-2202, Natural Gas (Methane) Sensor," Microsens SA, 4 pgs. (undated, believed to be prior to Dec. 20, 2010).

Barth, R. et al. "High-$T_c$ Air-bridge Microbolometers Fabricated by Silicon Micromachining Technique," Microelectronic Engineering, vol. 27, pp. 499-502 (1995).

Neda, T., et al. "A Polysilicon Flow Sensor for Gas Flowmeters"; Tranducers '95, Eurosensors IX; $8^{th}$ Intl. Conf. on Solid-State Sensors and Actuators and Eurosensors IX, pp. 548-551 (1995).

e2v Technologies, "Pellistor Application Note 5—Thermal Conductivity Sensors," A1A-Pellistor AN5 Issue 1, 2 pgs. (Mar. 2007).

POSiFA Microsystems Inc., "Thermal Conductivity Gas Sensor Die," 4 pgs. (2008).

Datasheet, "NAP-21A", Nemoto & Co., Ltd., retrieved from the Internet on Jul. 11, 2012 at http://www.nemoto.co.jp/en/products/sensor/manual/nap-21a.html, 1 pg. (2008).

Datasheet, "Orbisphere TC Sensor Selective Gas Measurement," Product Informatino, Process Analysis, Thermal Conductivity Sensor, Orbisphere 31XXX, Hach Lange, 2 pgs. (Dec. 2009).

Extended European Search Report for European Patent Appln. No. 11177642.3 (Feb. 24, 2012).

Research Institute of Innovative Technology for the Earth; "Development of New Amine Absorbents in COCS project"; Lyon, France; 17 pages (May 24, 2007).

Nemoto Sensor Engineering Co., Ltd.; "Residential Sensors—NAP-21A"; Tokyo, JP; 1 page (Nov. 2012).

Gattuso, Stephen A.; "Carbon Dioxide Capture by Tertiary Amidine Functional Adsorbents"; Thesis, Duquesne University; 66 pages (2003).

* cited by examiner

GAS SENSOR

CROSS-REFERENCE TO RELATED APPLICATIONS

This application claims the priority under 35 U.S.C. §119 of European patent application no. 11177642.3, filed on Aug. 16, 2011, the contents of which are incorporated by reference herein.

BACKGROUND OF THE INVENTION

This invention relates to a gas sensor. In particular, this invention relates to a gas sensor provided on a semiconductor substrate.

Gas sensors are used in a number of different applications to sense the composition and/or concentration of various gases. One example application is in the field of supply chain monitoring, in which the levels of $CO_2$ present in the air surrounding consumables such as food or beverages is monitored to determine suitability for consumption. The monitoring may typically be carried out at various stages in the distribution chain. Other applications include air quality monitoring, use in heating, ventilation and air conditioning (HVAC) system in buildings or automobiles, or $CO_2$ monitoring in greenhouses.

FIG. 1 illustrates a first example of a known kind of gas sensor 20. The sensor 20 is provided on a semiconductor substrate 2 (typically silicon), and includes an elongate sensor element 4 provided in the form of a meander line. The sensor element 4 is terminated at either end by a pair of electrical contacts 10, allowing an electrical current to be passed through the sensor element 4 during operation. The sensor element 4 is situated on an upper surface of a bridge structure 6, which extends across an opening 8 in the substrate 2. The bridge structure 6 itself comprises a thin membrane fabricated by under-etching a portion of the surface of the substrate 2 to form the opening 8. As illustrated in FIG. 1, the sensor element 4 has an upper surface that is exposed to the surrounding environment, allowing the sensor element 4 to come into contact with a gas to be sensed.

Also provided on the substrate 2 is a heater. The heater is includes a resistive element 14 through which a current is passed via a pair of electrical terminals 12. The resistive element 14 in this example is also provided in the form of a meander line. The purpose of the heater 14 in this example is to compensate for changes in ambient temperature by acting as a reference resistance.

The gas sensor 20 operates as follows. The sensor is first brought into contact with a gas to be sensed. It is noted that the gas may in some examples comprise a mixture of constituents. In such examples, the gas sensor can be used to determine the composition of the gas by determining the relative concentrations of the constituents (a common example being the concentration of $CO_2$ present in air).

To determine the concentration of the gas present, a current is passed through the sensor element 4 via the terminals 10. This causes the sensor element 4 to heat up. The rate at which heat can be carried away from the sensor element 4 by the surrounding gas is proportional to the thermal conductivity of the gas, which in turn is proportional to the concentration/composition of the gas. Accordingly, for a given gas concentration/composition, the heated sensor element 4 will reach thermal equilibrium at a certain corresponding temperature. This equilibrium temperature can be determined by measuring the resistance of the sensor element 4. In summary therefore, measurement of the resistance of the sensor element 4 can be used to determine the concentration/composition of gas that is in the vicinity of the sensor element 4.

As noted above, the sensor element 4 is provided in the form of a meander line. This increases the sensitivity of the gas sensor 20 by increasing the surface area of the sensor element 4 within the constraints of the space that is available for the sensor element 4 on the bridge structure 6. Nevertheless, the overall sensitivity of the gas sensor 20 is limited by the overall size and surface area of the sensor element 4 available for contact with the gas.

A second example of a gas sensor 30 is shown in FIGS. 2a and 2b. FIG. 2b shows a cross section of the gas sensor 30 through the line I in FIG. 2a. In this example, the gas sensor 30 includes a sensor element 34 located on a semiconductor substrate 2. The sensor element 34 comprises a metallic resistive element in the form of a meander line, and is produced using known metallisation techniques for semiconductor wafer processing. The formation of the sensor element 34 can be integrated with the formation of other metallisation features (e.g. power or signal lines) in the substrate 2 during manufacture. These additional features 32 are shown schematically below the sensor element 34 in FIGS. 2a and 2b.

The operation of the gas sensor 30 shown in FIGS. 2a and 2b is much the same as that described above in relation to the example of FIG. 1.

As shown in FIGS. 2a and 2b, an area 38 of the substrate 2 corresponding to the centre of the meander line of the sensor element 34 has been removed by etching. In principle, this increases the sensitivity of the sensor element 34 by exposing the side walls thereof, thereby increasing the surface area of the sensor element 34 that is available for contact with the gas to be sensed. Nevertheless, the sensitivity of the gas sensor is still limited by the overall size and surface area of the sensor element 34.

JP 2005/003468 describes a flow sensor comprising a resistor supported at either end of a meander line arrangement.

U.S. Pat. No. 5,597,953 describes a gas moisture sensor having a window on which a tape heater in the shaped of a meander line is provided. The tape heater is coated with a moisture sensitive layer.

U.S. Pat. No. 4,349,808 and a paper by R. Batha et al. entitled "High-$T_c$ air-bridge microbolometers fabricated by silicon micromachining technique" published in Microelectronic Engineering 27 (1995) p. 499-502, do not describe gas sensors, but instead relate to bolometers.

JP 6,118,046 describes an atmosphere sensor comprising a heating resistor arranged on a bridged thin film insulator. US 2004/251117 describes a suspended thin film resistor.

U.S. Pat. No. 5,753,916 describes a detector for an infrared gas analyzer, and U.S. Pat. No. 5,756,878 describes a thermal conductivity measuring device. Neither of these documents relate to a gas sensor of the kind provided on a semiconductor substrate.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a gas sensor on a semiconductor substrate. The gas sensor includes an elongate sensor element extending across an opening and has first and second opposed surfaces exposed for contact with a gas to be sensed. The first surface faces away from a major surface of the substrate. The second surface faces toward the major surface. The electrical conductivity of the elongate sensor element is sensitive to a composition and/or concentration of the gas to which the opposed first and second surfaces are exposable. The gas sensor also includes a support structure arranged to increase the mechanical robustness of the gas sensor by supporting the elongate sensor element in the opening.

Since the sensor element has multiple surfaces available for sensing the presence of a gas, the sensitivity of the gas sensor is enhanced. To mitigate against the relative structural weakness of the sensor element that may otherwise result from the relatively large proportion of the sensor element that is free hanging (that is to say, separated from its surroundings), a support structure is provided to add mechanical strength.

The support structure can include at least one elongate strut that extends across the opening.

The elongate sensor element can be arranged in a meander line. In such examples, the one of more of the at least one elongate struts of the support structure can extend substantially perpendicular to a long axis of the meander line.

At least part of the support structure can extend outwardly from the substrate to support the sensor element at the first surface (namely the surface of the sensor element that faces the substrate. In this way, the support structure can provide support from beneath the sensor element. In other examples, the sensor can be supported from above. In such examples, the sensor can be suspended from the support structure above the semiconductor substrate. These two approaches can also be combined, whereby support can be provided from both above and below the sensor element.

The support structure can be provided as one or more patterned layers on the semiconductor substrate, allowing the structure itself to be provided in a manner compatible with known semiconductor processing techniques.

The support structure can comprise any suitable material, examples being SiC, SiN, SiO2, Si, GeO2, GeN or a polymer. The sensor element itself can be electrically conductive e.g. metallic. Suitable materials include Cu, Al, W, WC, TiN, TaN, doped polysilicon, Ti, Ta, Pt, Ag or Au.

According to another aspect of the invention, there is provided a semiconductor device including a plurality of sensors integrated in a semiconductor die or package. At least one of the plurality of sensors is a gas sensor of the kind described above.

According to a further aspect of the invention, there is provided a radio frequency identification (RFID) tag including a gas sensor of the kind described above. The gas sensor may be included in a semiconductor device having a plurality of sensors integrated in a semiconductor die or package as described above.

According to a further aspect of the invention, there is provided a mobile communications device comprising the gas sensor of the kind described above. Examples of mobile communications devices include mobile telephones, laptops and tablet computers.

According to another aspect of the invention, there is provided a heating, ventilation and air conditioning (HVAC) system comprising one or more gas sensors comprising the gas sensor of the kind described above. In particular, the HVAC system can be the HVAC system of an automobile (e.g. car, van, truck). In another example, the HVAC system can be the HVAC system in a building such as a house, office or warehouse. When used in a HVAC system, the gas sensor can monitor gas concentrations for determining air quality. A further envisaged application is for monitoring $CO_2$ and or other gases in green houses or in smart buildings.

According to another aspect of the invention, there is provided use of the gas sensor described above, the semiconductor device described above, or RFID tag described above, in the field of supply chain monitoring.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Embodiments of the invention provide a gas sensor on a semiconductor substrate. Integration of gas sensors on a substrate in this way allows the sensors to be produced in large numbers at relatively low cost. In principle, standard semiconductor processes such as deposition, lithographic and etching techniques can be applied to manufacture the sensor. These techniques include the use of known metallization techniques for constructing features of the sensor such as the sensor element and terminals.

Although semiconductor processing of this kind allows mass production, the resulting sensors should also meet requirements relating to mechanical robustness, in order that they can find use in applications such as supply chain monitoring.

Embodiments of this invention provide a gas sensor with a relatively high degree of sensitivity. As described herein, this can be achieved by the provision of an elongate sensor element that extends across an opening in a semiconductor substrate.

The relatively large surface area of the described elongate sensor element enhances the sensitivity of the sensor, since a large area is made available for heat exchange with a surrounding gas.

In view of its elongate form and the manner in which it extends across the opening (e.g. instead of resting on a surface such as the surface of the bridge structure described above in relation to FIG. 1), the described sensor element may be prone to mechanical weakness. To mitigate against this potential weakness, in accordance with an embodiment of the invention, the elongate sensor element is provided with a support structure. The support structure supports the elongate sensor element in the opening, adding mechanical strength to the overall sensor. Various example configurations of the elongate sensor element and its support structure are described below.

Figure 3A:
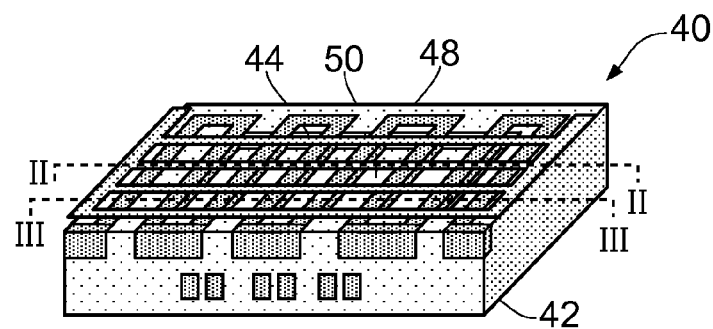
FIGS. 3a-3c show a gas sensor according to a first embodiment of the invention.
Figures 3B, 3C:
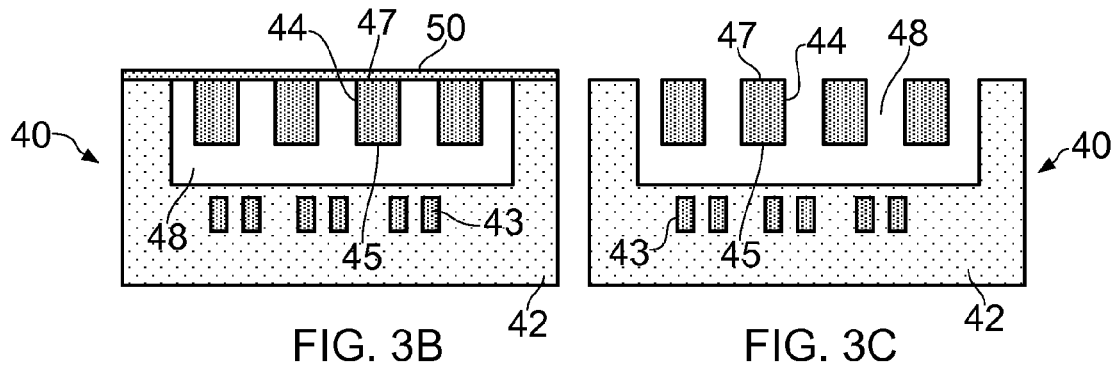

FIGS. 3a to 3c illustrate a gas sensor 40 in accordance with a first embodiment of the invention. FIGS. 3b and 3c illustrate cross sections through the gas sensor 40 at the positions indicated by the lines II and III shown in FIG. 3a.

As illustrated in FIGS. 3a to 3c, the gas sensor 40 is provided on a semiconductor substrate 42. The substrate may comprise, for example, silicon. The gas sensor 40 includes an elongate sensor element 44, which extends across an opening 48, which in this example is provided on an upper surface (major surface) of the substrate 42. As can be seen from FIGS. 3b and 3c, the elongate sensor element 44 has a first surface 47 and a second surface 45. The first surface 47 faces away from the major surface of the substrate 42, while the second surface 45 faces toward the major surface of the substrate 42. The first surface 47 may therefore be considered to be an upper surface of the sensor element 44, while the second surface 45 may be considered as a lower surface of the sensor element 44.

In FIG. 3c it is illustrated that both the first surface 47 and the second surface 45 of the elongate sensor element 44 are exposed. Note that in some embodiments, not all of the first and second surfaces are exposed. For example, the support structure 50 may partially cover one of said surfaces 47, 45 where it makes contact with the elongate sensor element 44. In the present embodiment, it can be seen from FIGS. 3a and 3b that the support structure partially covers the first surface 47. The configuration of the support structure 50 is described in more detail below.

In any event, because both surfaces 47, 45 are exposed, both surfaces 47, 45 can come into contact with a gas to be sensed. The associated increase in available surface area for contact with the gas to be sensed produces an increased sensitivity of the elongate sensor element 44 to the composition and/or concentration of the gas to be sensed.

As shown in FIGS. 3a and 3b, the gas sensor 40 includes a support structure 50. The support structure 50 supports the elongate sensor element 44 in the opening 48 on the substrate 42, whereby the mechanical robustness of the gas sensor 40 is improved. Accordingly, although the elongate sensor element 44 is largely "free hanging", the support structure 50 can prevent damage to the sensor 40 caused by external shocks (e.g. handling of goods or packages incorporating the sensor 40). In this example, the support structure 50 comprises a series of elongate struts that extend across the opening 48 in the substrate 42. Any suitable number of struts can be provided in accordance with design requirements. For example, in some embodiments, a single strut may suffice, while in other embodiments a plurality of struts may be provided for additional robustness/strength. In the present example shown in FIG. 3, the struts run substantially perpendicular to the long axis of the meander line adopted by the sensor element 44. In this regard, the long axis of the meander line is considered to be the axis along which the longest portions of the individual sections of the meander line extend.

In other examples, the support structure 50 may take alternative forms. For example, it is not considered essential that the support struts of the structure 50 run substantially perpendicular to the long axis of the meander line. In addition, the support structure may include struts that do not extend fully across the opening 48—for example, the support structure 50 may comprise a series of interdigitated fingers extending only part way across the opening 48.

The support structure 50 can comprise any suitable material, examples being SiC, SiN, SiO2, Si, GeO2, GeN or a polymer.

As shown in FIGS. 3a and 3b, in the present example, the support structure is located above the elongate sensor element 44 on the substrate 42, whereby the elongate sensor element 44 suspended from the support structure 50 in the opening 48. The elongate sensor element 44 is attached to the support structure 50 at certain (for example, regular) intervals to ensure that the elongate sensor element 44 is provided with a sufficient degree of support in accordance with design tolerances relating to the robustness of the gas sensor 40. While some of the first surface 47 of the elongate sensor element 44 is attached to the support structure 50 and therefore not available for contact with a surrounding gas, it is evident from FIG. 3a that much of the first surface 47 is nevertheless available for gas contact. In any event, the amount of surface area available on the first surface 47 that is available for gas contact is non-zero, in contrast to known designs described above, in which a surface (generally a lower surface (see, for example, FIGS. 1 and 2)) is completely sealed and therefore unavailable for gas contact. In accordance with an embodiment of the invention, it is envisaged that at least 50% of the surface adjacent to the support structure or to which the support structure is attached remains available for gas contact.

In the present example, it can be seen that some portions of the elongate sensor element 44 do not extend across the opening 48. Indeed, it is not considered essential that the entire elongate sensor element 44 extends across the opening 48. In particular, in the example shown in FIG. 3a, the turning points of the meander line formation of the elongate sensor element 44 are embedded within the substrate 42. This furthers adds to the structural strength of the gas sensor 40. In accordance with an embodiment of the invention, the support structure 50 provides mechanical support to those portions of the elongate sensor element 44 that do extend across the opening 48.

Figure 1:
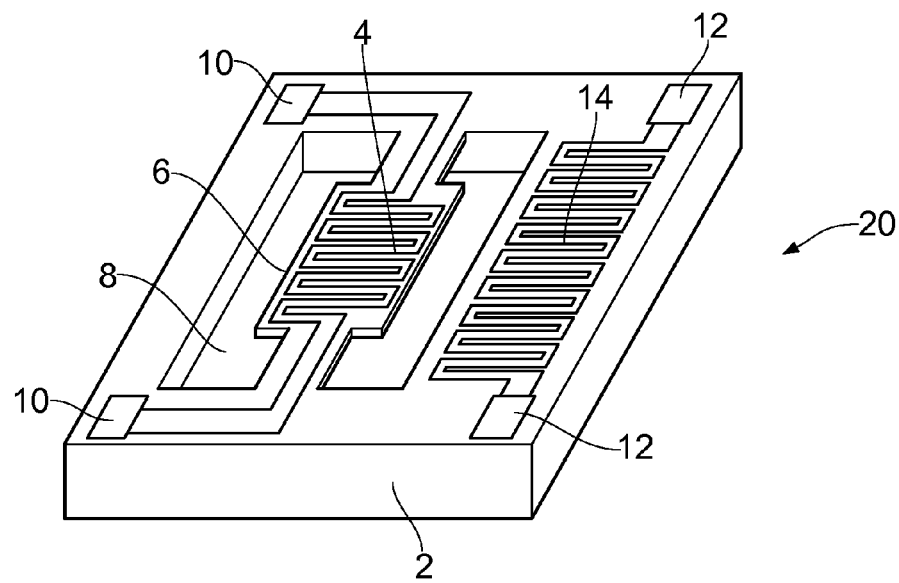
FIG. 1 shows a first example of a known gas sensor.
Figure 2A:
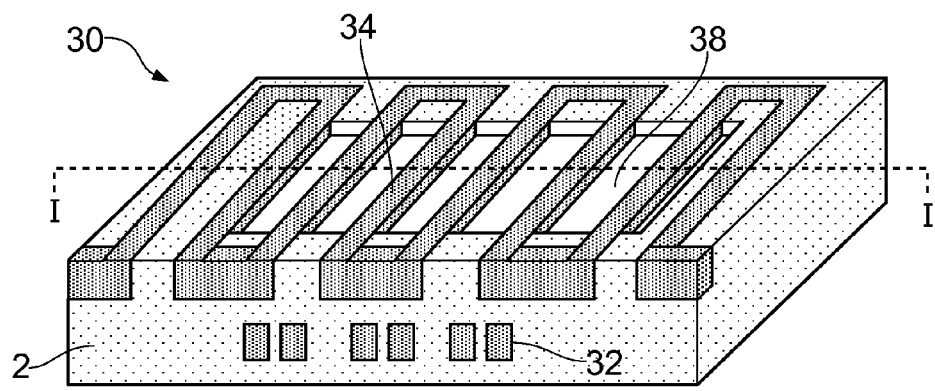
FIG. 2 shows a second example of a known gas sensor.
Figure 2B:
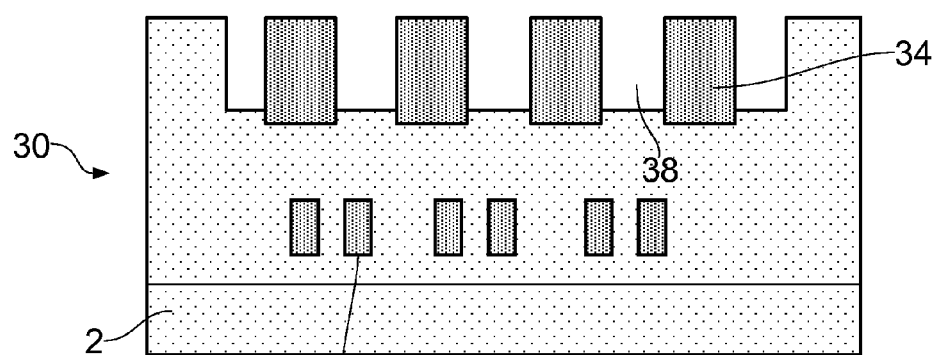

The elongate sensor element 44 can comprise any suitable material and the principal of operation of the sensor element itself will be similar to the operation of the sensor elements shown in FIGS. 1 and 2 and described above. Accordingly, the material used to construct the sensor element 44 should be electrically conductive to allow a current to pass through the sensor element 44 for heating it to a temperature at which thermal equilibrium with the surrounding gas is reached. Examples of suitable materials include conductive material such as doped polysilicon or metals and alloys such as Cu, Al, W, WC, TiN, TaN, Ti, Ta, Pt, Ag or Au.

The manufacture of a gas sensor 40 of the kind shown in FIG. 3 will be discussed herein below in relation to FIG. 5. It will be noted that FIG. 3 also illustrates that further metallization features 43 may be provided within the substrate 42, for example, beneath the opening 48. Accordingly, it is envisaged that the formation of the elongate sensor element 44 may take place as part of the metallization steps performed in processing of the semiconductor substrate 42 as a whole.

Figure 4A:
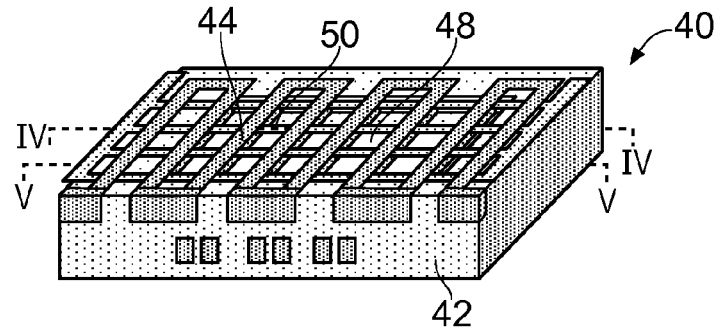
FIGS. 4a-4c show a gas sensor according to a second embodiment of the invention.
Figures 4B, 4C:
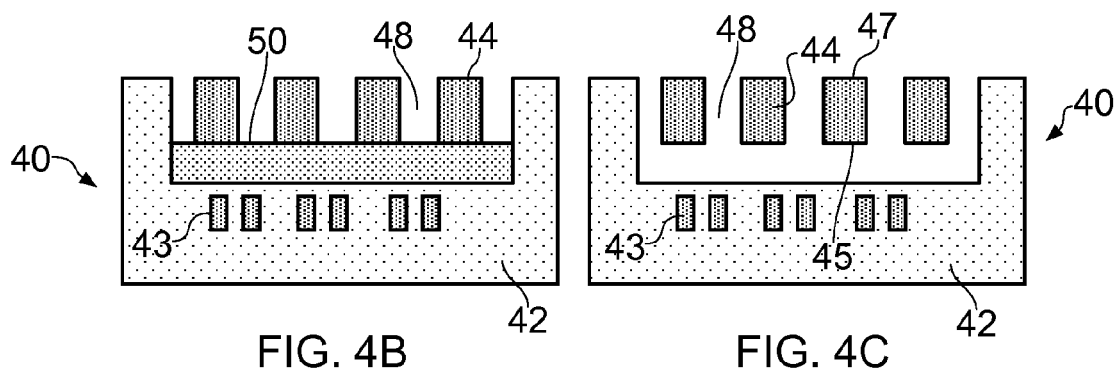

FIG. 4 illustrates a second example of a gas sensor 40 in accordance with an embodiment of the invention. FIGS. 4b and 4c illustrate cross sections through the gas sensor 40 along the lines IV and V shown in FIG. 4a, respectively.

The gas sensor 40 shown in FIG. 4 is similar to the gas sensor 40 shown in FIG. 3, except in the configuration of the support structure 50. In particular, the support structure 50 is not located adjacent to the first surface 47 of the elongate sensor element 44, but is instead provided adjacent to the second surface 45 of the elongate sensor element 44. Accordingly, in this example, the support structure supports the elongate sensor element 44 from "beneath", extending as it does outwardly from the substrate 42 towards the second surface 45.

The configuration of the support structure 50 itself in terms of shape and formation in the example of FIG. 4 are nevertheless similar to the configuration and formation shown in FIG. 3. Accordingly, in this example, the support structure 50 includes a series of elongate struts which extend substantially perpendicular to the long axis of the meander line of the sensor element 44 to provide support at intervals along the meander line within the opening 48 in the substrate 42. As described above in relation to FIG. 3 however, the exact group configuration of the support structure in terms of shape and formation can be varied in accordance with design requirements.

FIGS. 5a to 5f illustrate an example of a method of making a gas sensor in accordance with an embodiment of the invention. In particular, the method illustrated in FIG. 5 is suitable for the manufacture of the embodiment shown in FIG. 3. It will be appreciated that similar methodologies may be used for the manufacture of the gas sensor embodiment shown in FIG. 4.

In each of FIGS. 5a to 5f, there is shown a cross section of the gas sensor through the dotted lines VI to XI, respectively.

Figure 5A:
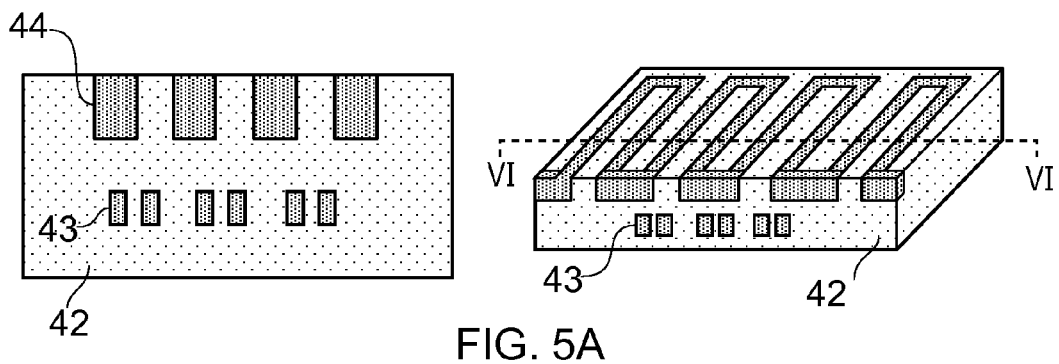
FIGS. 5a-5f show a method of making a gas sensor in accordance with an embodiment of the invention.

The first stage in making a gas sensor in accordance with an embodiment of this invention is illustrated in FIG. 5a. In this stage, there is provided a semiconductor substrate 42 upon which a number of metallization steps have been performed to provide metallization features such as power and signal lines 43. Similarly, these metallization steps, which are well known in the art for building up a series of metallization layers on a substrate, can be used to produce an elongate sensor element 44 located substantially at the major surface of the substrate 42. The metallization techniques that can be used to produce the features 42 and the sensor element 44 include lithographic, etching and planarization techniques. These techniques are well known in the art and will not be elaborated on further herein.

Figure 5B:
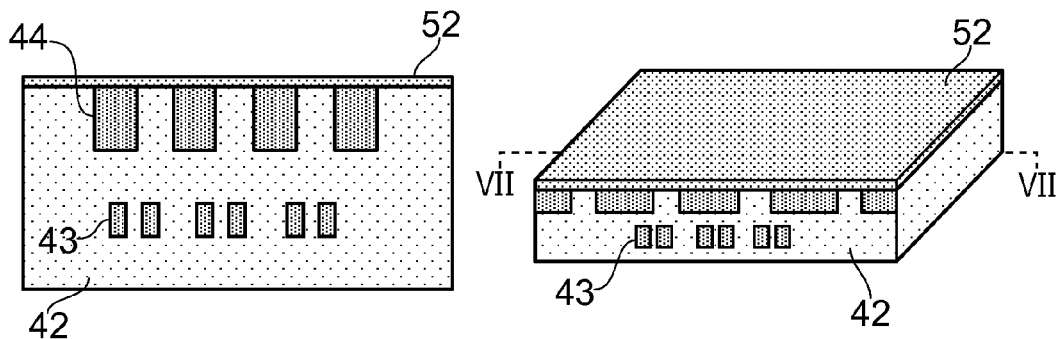

A next stage of the manufacture process is shown in FIG. 5b. In this stage, a layer 52, which will subsequently form the support structure 50 for the elongate sensor element 44 is deposited over the major surface of the substrate 42.

Figure 5C:
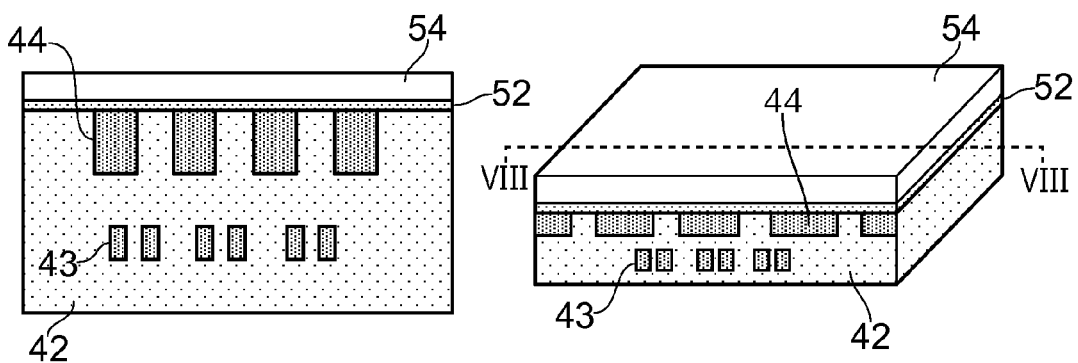
Figure 5D:
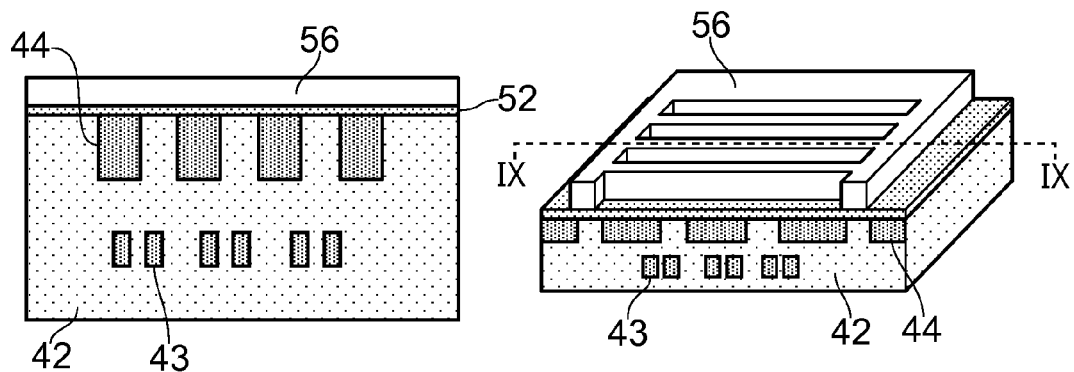
Figure 5E:
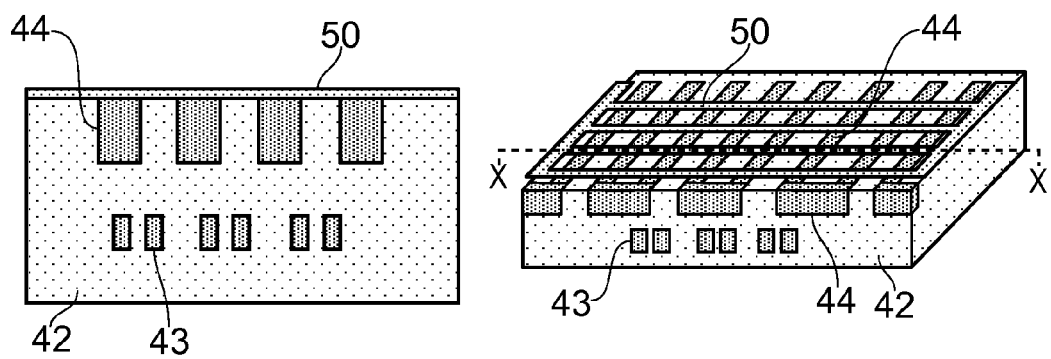

In a next stage shown in FIG. 5c, a mask layer 54 is deposited over the layer 52. Subsequently, the layer 54 is patterned using, for example, lithographic and etching techniques to produce a patterned mask 56 (FIG. 5d). The layer 52 is then etched through the patterned mask 56 to produce a support structure having the desired formation. In the present example, as shown in FIG. 5e, the formation of the support structure 50 is analogous to the formation described above in relation to FIG. 3. Accordingly, the support structure 50 includes a number of elongate struts which extend substantially perpendicular to a long axis of the meander line of the elongate sensor element 44.

Thereafter, the mask 56 is removed and a further etching step is performed to create an opening 48 in the surface of the substrate 42. The creation of the opening 48 may be achieved using a further mask to prevent inadvertent etching of undesired portions of the major surface of the substrate 42.

Figure 5F:
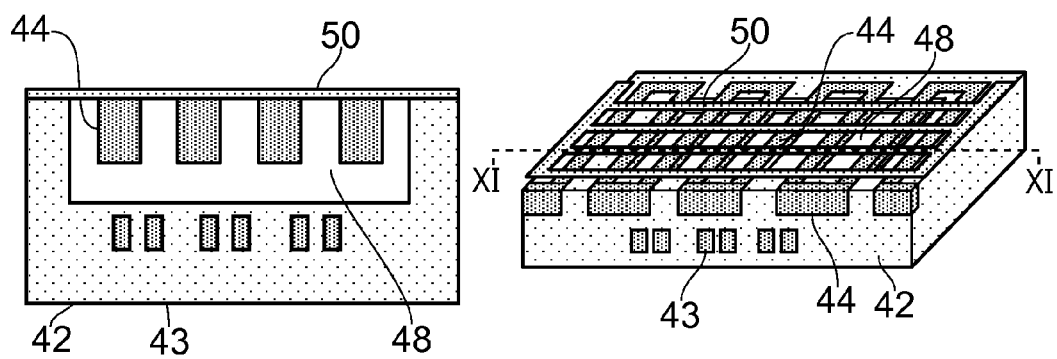

As illustrated in FIG. 5f, the etching step used to create the opening 48 selectively removes material of the substrate 42 around the elongate sensor element 44. Accordingly, as shown in FIG. 5f, and in particular in the cross section view of FIG. 5f, the side walls and underside of the elongate sensor element 44 corresponding to the second surface 45 described above in FIG. 3 become exposed for contact with a surrounding gas. It will be clear to the person skilled in the art that the upper surface of the elongate sensor element 44 corresponding to the surface 47 described above in FIG. 3 is already largely available for contact with a surrounding gas, albeit that the portions of the upper surface of the elongate sensor element 44 which are attached to the support structure 50 are not so exposed.

Any suitable etching technique can be used to form the opening 48. Examples include either wet or dry etching techniques such as BHF or vapour HF treatments. To prevent inadvertent over etching of the material of the substrate 42 when producing the opening 48, an etch stop layer may optionally be provided within the substrate at a location corresponding substantially to the lower surface of the opening 48. Alternatively, the etching process may be timed to prevent inadvertent over etching which may, for example, expose features beneath the opening 48 such as the metallization features 43.

As mentioned above, it will be appreciated that the method described in FIG. 5 can be adapted to produce other configurations in accordance with a gas sensor of the present invention. For example, to produce a gas sensor of the kind illustrated in FIG. 4, the layer corresponding to the support structure 50 can be patterned upon the substrate 42 in advance of deposition of the metallization layers associated with the elongate sensor element 44. Following formation of the elongate sensor element 44 using these normal metallization techniques, a selective etch step can be used to create the opening 48 in the major surface of the substrate 42, thereby arriving at the configuration of the device described in relation to FIG. 4.

Figure 6:
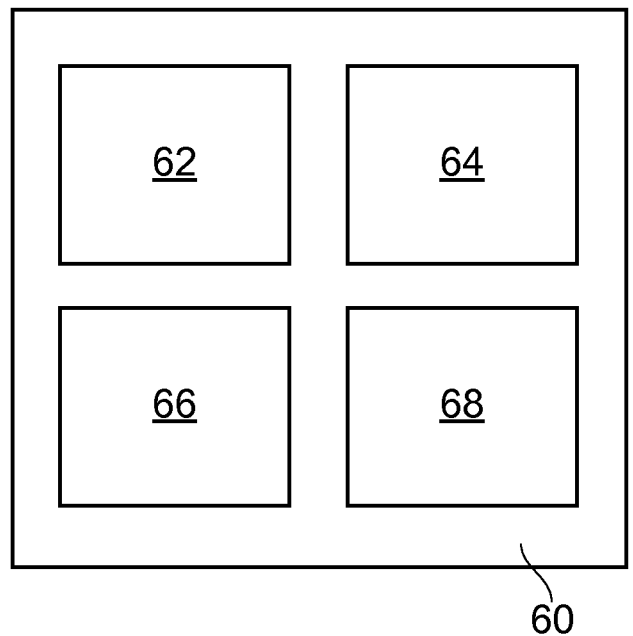
FIG. 6 shows a semiconductor device comprising a plurality of sensors integrated in a semiconductor die or package, in accordance with an embodiment of the invention.

FIG. 6 illustrates an example of a semiconductor device comprising a plurality of 62, 64, 66, 68 of sensors integrated in a semiconductor die 60 in accordance with an embodiment of the invention.

In this example, at least one of the sensors 62, 64, 66 or 68 comprises a gas sensor according to an embodiment of the invention. Accordingly, it is envisaged that a gas sensor (for example, a gas sensor of the kind described above in relation to FIGS. 3 and 4) may form one of a plurality of different sensors integrated into a single semiconductor die. Alternatively, it is also envisaged that the different sensors may be provided on separate dies incorporated into a single package. In this way, a diverse range of sensor functionality can be integrated into a single semiconductor device. For example, in addition to the provision of at least one gas sensor, other sensors such as humidity, pH, ambient light, pressure, flow, temperature or further gas sensors could be provided in a single die or package.

Figure 7:
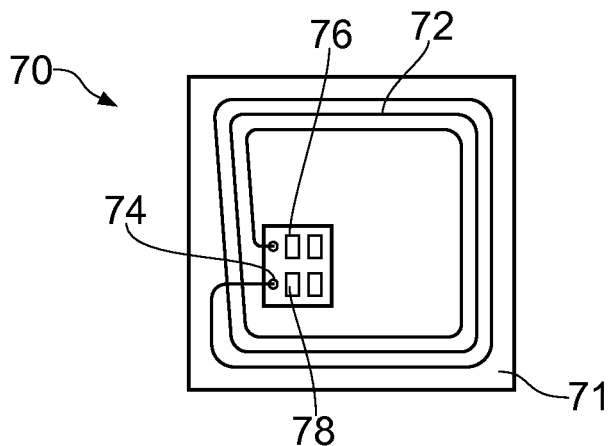
FIG. 7 shows a radio frequency identification (RFID) tag in accordance with an embodiment of the invention.

FIG. 7 illustrates a radio frequency identification (RFID) tag 70 in accordance with an embodiment of the invention. In this embodiment, either a gas sensor of the kind described above or alternatively a semiconductor die or package 60 as described above in relation to FIG. 6 is provided on a carrier 71 along with other features normally associated with RFID tags such as an induction loop 42 which may be terminated 74 with the die or package carrying the sensor or sensors 78.

Figure 8:
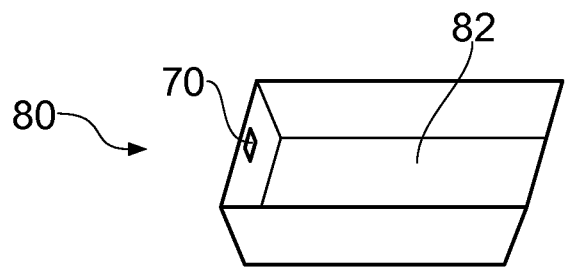
FIG. 8 shows a container for holding consumables such as food, the container incorporating an RFID tag in accordance with an embodiment of the invention.

The provision of a gas sensor in an RFID tag 70 allows for convenient read outs of measurements collected by the gas sensor in applications such as supply chain monitoring. For example, in FIG. 8, there is shown a food container 80 having an area 82 in which consumables such as food can be placed. Also within the area 82, for example attached to a side wall defining the area 82, there is provided an RFID tag 70 of the kind shown in FIG. 7. FIG. 8 accordingly illustrates that a gas sensor in accordance with an embodiment of the present invention can be used in the field of supply chain monitoring, for monitoring the suitability of food for consumption.

As described above, in addition to applications in supply chain monitoring, a gas sensor according to an embodiment of the invention can be find use in a HVAC system in an automobile or building (e.g. to monitor air quality). A gas sensor according to an embodiment of the invention can also be used to monitor gas ($CO_2$) levels in greenhouses.

Accordingly, there has been described a gas sensor on a semiconductor substrate. The gas sensor includes an elongate sensor element extending across an opening and has first and second opposed surfaces exposed for contact with a gas to be sensed. The first surface faces away from a major surface of the substrate. The second surface faces toward said major surface. The electrical conductivity of the elongate sensor element is sensitive to a concentration of said gas to which the opposed first and second surfaces are exposable. The gas sensor further includes a support structure arranged to increase the mechanical robustness of the gas sensor by supporting the elongate sensor element in the opening.

Although particular embodiments of the invention have been described, it will be appreciated that many modifications/additions and/or substitutions may be made within the scope of the claimed invention.

The invention claimed is:

1. A gas sensor on a semiconductor substrate, the gas sensor comprising:
    an elongate sensor element extending across an opening and having first and second opposed surfaces exposed for contact with a gas to be sensed, wherein the first surface faces away from a major surface of the substrate, wherein the second surface faces toward said major surface, and wherein an electrical conductivity of the elongate sensor element is sensitive to at least one of a composition and a concentration of said gas to be sensed; and
    a support structure directly exposed to the opening, and attached to the first surface of the sensor element at regular intervals over the opening, such that over the opening the sensor element is not continuously attached to the support structure, wherein a majority of the first surface of the sensor element remains available for gas contact while attached to the support structure.

2. The gas sensor of claim 1, wherein the support structure comprises at least one elongate strut extending across the opening.

3. The gas sensor of claim 1, wherein the elongate sensor element is arranged in a meander line.

4. The gas sensor of claim 3, wherein the support structure comprises at least one elongate strut extending across the opening and wherein the at least one elongate strut extends substantially perpendicular to a long axis of the meander line.

5. The gas sensor of claim 1, wherein at least part of the support structure extends outwardly from the substrate to support the sensor element at the first surface.

6. The gas sensor of claim 1, wherein the sensor element is suspended from the support structure above the semiconductor substrate.

7. The gas sensor of claim 1, wherein the support structure comprises a patterned layer on the semiconductor substrate.

8. The gas sensor of claim 1, wherein the support structure comprises any of SiC, SiN, $SiO_2$, Si, $GeO_2$, GeN and a polymer.

9. The gas sensor of claim 1, wherein the sensor element is metallic.

10. The gas sensor of claim 9, wherein the sensor element comprises one of Cu, Al, W, WC, TiN, TaN, Ti, Ta, Pt, Ag and Au.

11. A semiconductor device comprising a plurality of sensors integrated in one of a semiconductor die and a package, wherein at least one of the plurality of sensors comprises the gas sensor according to claim 1.

12. The gas sensor of claim 1, wherein the gas sensor is configured for use in a radio frequency identification (RFID) tag.

13. The gas sensor of claim 1, wherein the gas sensor is configured for use in a mobile communications device.

14. The gas sensor of claim 1, wherein the gas sensor is configured for use in a heating, ventilation and air conditioning (HVAC) system.

15. A gas sensor on a semiconductor substrate, the gas sensor comprising:
    an elongate sensor element extending across an opening and having first and second opposed surfaces exposed for contact with a gas to be sensed, wherein the first surface faces away from a major surface of the substrate, wherein the second surface faces toward said major surface, and wherein an electrical conductivity of the elongate sensor element is sensitive to at least one of a composition and a concentration of said gas to be sensed; and
    a support structure attached to the second surface of the sensor element and extending outwardly from the substrate towards the second surface, such that over the opening the sensor element is not continuously attached to the support structure, wherein a majority of the second surface of the sensor element remains available for gas contact while attached to the support structure.

* * * * *